(12) United States Patent
Scott

(10) Patent No.: US 7,927,875 B1
(45) Date of Patent: Apr. 19, 2011

(54) MOISTURE AND SEDIMENT ANALYSIS

(75) Inventor: Bentley N. Scott, Garland, TX (US)

(73) Assignee: Phase Dynamics, Inc., Richardson, TX (US)

( * ) Notice: Subject to any disclaimer, the term of this patent is extended or adjusted under 35 U.S.C. 154(b) by 0 days.

(21) Appl. No.: 12/653,596

(22) Filed: Dec. 16, 2009

Related U.S. Application Data

(62) Division of application No. 11/046,534, filed on Jan. 28, 2005, now Pat. No. 7,648,836.

(60) Provisional application No. 60/539,703, filed on Jan. 28, 2004.

(51) Int. Cl.
*G01N 33/18* (2006.01)
(52) U.S. Cl. ............... 436/39; 436/40; 73/73; 73/76
(58) Field of Classification Search .................. 436/39, 436/40; 73/61.43, 73, 76
See application file for complete search history.

(56) References Cited

U.S. PATENT DOCUMENTS

| | | | | |
|---|---|---|---|---|
| 270,489 | A | * | 1/1883 | Schubert .................. 73/61.65 |
| 1,718,590 | A | | 6/1929 | Smith |
| 3,528,775 | A | * | 9/1970 | Siegfriedt et al. ............. 436/40 |
| 3,745,659 | A | * | 7/1973 | Hsu ....................... 33/720 |
| 3,942,360 | A | * | 3/1976 | Wada ..................... 73/61.72 |
| 4,004,453 | A | | 1/1977 | Thyrum |
| 4,996,490 | A | | 2/1991 | Scott et al. |
| 5,656,767 | A | | 8/1997 | Garvey, III et al. |
| 6,593,753 | B2 | | 7/2003 | Scott et al. |
| 6,810,719 | B2 | | 11/2004 | Dutton et al. |
| 2005/0011892 | A1 | | 1/2005 | Nakajima et al. |

OTHER PUBLICATIONS

Parviz Mehdizadeh, et al., "Wet Gas Metering: Trends in Applications and Technical Developments", Society of Petroleum Engineers, Presented at the SPE Annual Technical Conference and Exhibition held in San Antonio, Texas, Sep. 29-Oct. 2, 2002, 14 pages.

* cited by examiner

*Primary Examiner* — Robert J Hill, Jr.
*Assistant Examiner* — Dwan A Gerido

(57) ABSTRACT

Systems and methods for measuring the moisture and sediment content of a sample. In one embodiment, a sample to be tested is collected in a field bottle. The sample from the field bottle is then transferred from the field bottle, and into and through an analysis bottle containing a desiccant material. As the sample is being pulled through the analysis bottle, a microwave measurement system (or other scattering parameter measuring system) is used to measure the effects of the sample on the scattering parameters of the desiccant material. By measuring the effects of the sample on the scattering parameters of the desiccant material, the sample's moisture content can be determined. The sample's moisture can also be determined by measuring the expanded volume of the desiccant. A filter section having a sight glass with graduations is used to determine the sediment content of the sample.

5 Claims, 10 Drawing Sheets

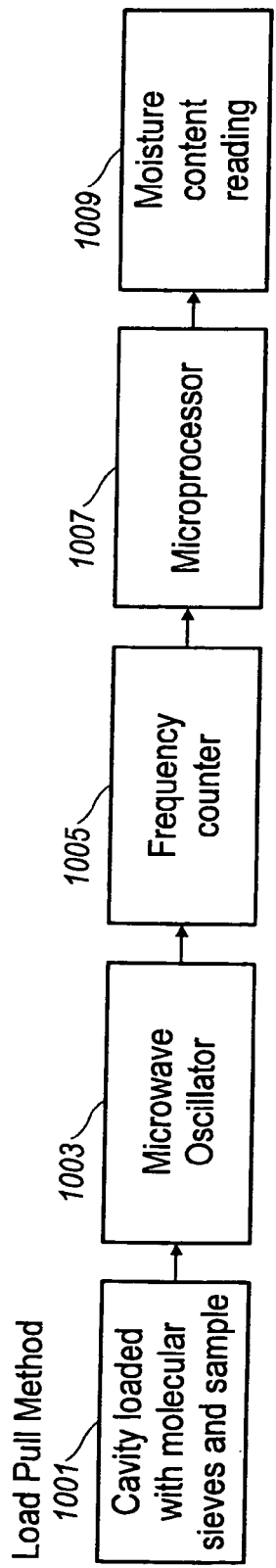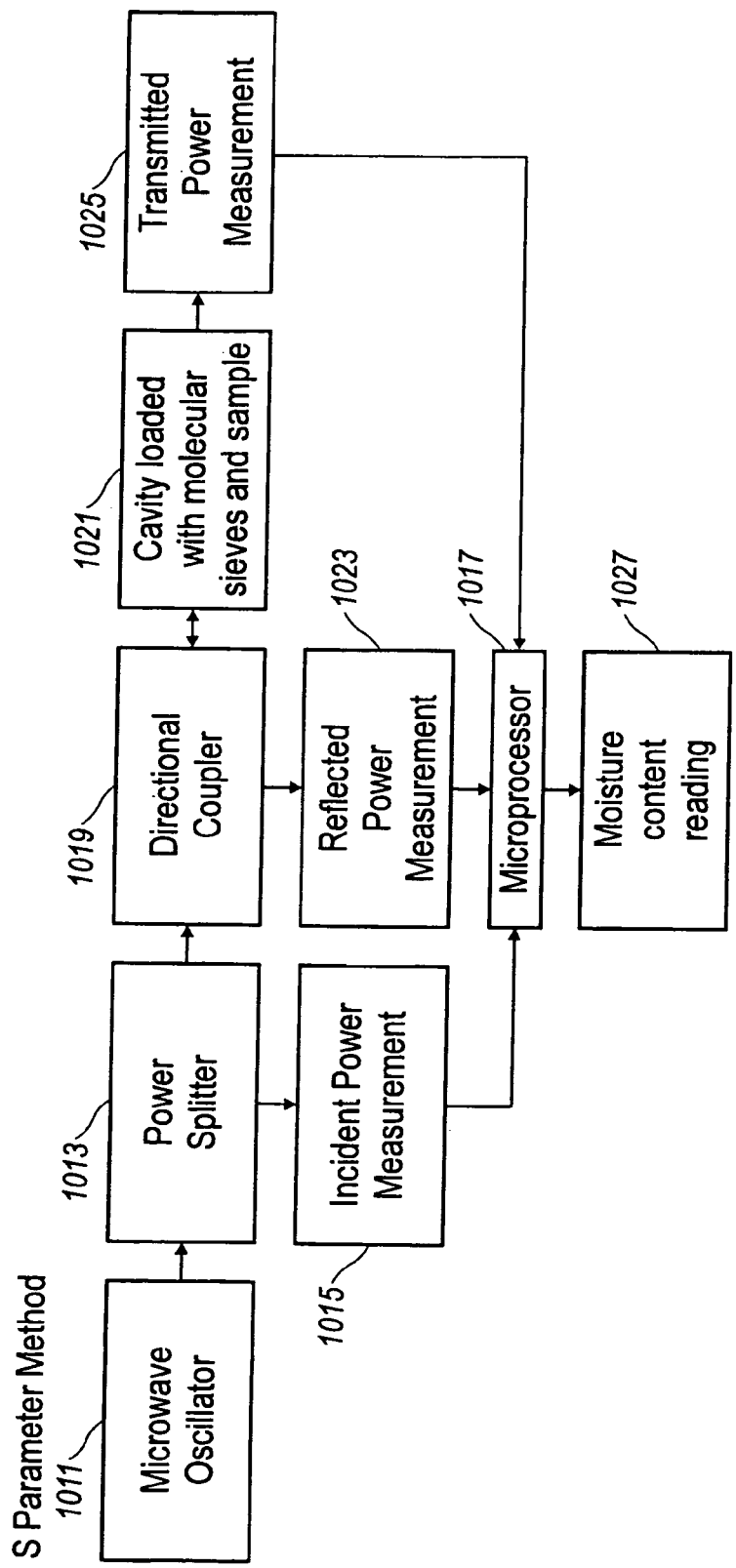

MOISTURE AND SEDIMENT ANALYSIS

CROSS-REFERENCE TO RELATED APPLICATIONS

This application is a divisional application of U.S. application Ser. No. 11/046,534 filed on Jan. 28, 2005. U.S. application Ser. No. 11/046,534 was issued as U.S. Pat. No. 7,648,836 on Dec. 30, 2009. U.S. application Ser. No. 11/046,534 claims priority from U.S. Provisional Application 60/539,703 filed 28 Jan. 2004. This application claims priority to both U.S. application Ser. No. 11/046,534 and U.S. Provisional Application 60/539,703, both of which are hereby incorporated by reference as if fully set forth herein.

BACKGROUND AND SUMMARY OF THE INVENTION

The present inventions relate generally to a laboratory or portable measurement method and system, and more particularly, to a method and system for the point of sale measurement of the water and sediment content in a petroleum sample.

Conventional Methods for Measuring Water Content

A determination of water content in crude oil is required to measure accurately net volumes of actual oil in sales, taxation, exchanges, and custody transfers. The water content of crude oil is also significant because it can cause corrosion of equipment and problems in processing. Thus, various methods have been developed for measuring the water content of crude oil.

Karl Fischer Titration Method

In 1935, German scientist, Karl Fischer, developed a titrimetric determination of water content using a reagent that contained iodine, sulphur dioxide, anhydrous pyridine and anhydrous methanol. This method can be subdivided into two main techniques: volumetric titration and coulometric titration.

The volumetric technique involves dissolving the sample in a suitable solvent and adding measured quantities of a reagent containing iodine until an end point is reached. This end point is determined potentiometrically using a platinum electrode. When all of the water has reacted, the platinum measuring indicator electrode will electronically instruct the burette to stop dispensing. The volume of KF reagent dispensed is recorded. Based on the concentration of iodine in the KF reagent, the amount of water present is then calculated.

However, even with the automatic or semi-automatic instruments commercially available, there are certain problems associated with this technique. These problems include long analysis time, required reagent calibration, and high reagent consumption rate.

In the coulometric technique developed by Meyer and Boyd in 1959, the sample is introduced into a mixture of pyridine/methanol that contains iodide ions and sulphur dioxide. The electrode system consists of an anode and cathode platinum electrodes that conduct electricity through the cell. Iodine is generated at the anode and reacts with any water present. The production of iodine is directly proportional to the amount of electricity according to Faraday's Law as shown in the equation:

$$2I^- - 2e \rightarrow I_2.$$

According to the stoichiometry of the reaction, 1 mole of iodine will react with 1 mole of water, and combining this with coulometry, 1 milligram of water is equivalent to 10.71 coulombs of electricity. Therefore, it is possible to directly determine the amount of water present in a sample by measuring the electrolysis current in coulombs. The platinum indicating electrode voltametrically senses the presence of water and continues to generate iodine until all the water in the sample has been reacted.

From this titration, the onboard microprocessor calculates the total amount of current consumed in completing the titration and the time to completion in seconds. Based on the relationship between coulombs and iodine, the exact amount of iodine generated is recorded. Since water reacts in the 1:1 ratio with iodine, the amount of water can be calculated.

Although the original Karl Fischer reagent contained pyridine, most reagent manufacturers now use other amines such as imidazol.

Karl Fischer titration is one of the most widely used techniques for measuring the water content in a large range of samples. However, it has limits that affect its usefulness. For example, it utilizes hazardous reagents that require the operator to exercise care in the storing, handling, and disposing of reagents that degrade with time. With the techniques, a total sample size of 0.5 ml. or smaller is taken from a larger sample size, typically 250 ml. The small sample size utilized by the techniques causes errors and cannot measure water percentages over 1% accurately. Also, the Karl Fischer titration techniques are operator intensive and do not provide any information with regard to the amount of sedimentation in a sample.

(Please see *Manual of Petroleum Measurement Standards*, Chapter 10.7—*Standard Test Method for Water in Crude Oils by Potentiometric Karl Fischer Titration* and Chapter 10.9—*Determination of Water in Crude Oils Coulometric Karl Fischer Titration* for the complete protocols, which are hereby incorporated by reference.)

Centrifuge Method

In the standard method for determining the water content in crude oil by centrifuge, equal volumes of a sample and water saturated toluene are placed into two cone-shaped centrifuge tubes. The tubes are then corked and placed into a centrifuge. The tubes are then spun for 10 minutes at a minimum relative centrifugal force of 600 calculated from the following equation:

$$rmp = 1335\sqrt{rcf/d}$$

where:
  rcf=relative centrifugal force and
  d=diameter of swing measured between tips of opposite tubes when in rotating position, mm.

Immediately after the centrifuge comes to rest following the spin, the combined volume of water and sediment at the bottom of each tube is read and recorded. The spin is then repeated until the combined volume of water and sediment remains constant for two consecutive spins. The final volume of water is then recorded for each tube.

The standard method for determining the water content by centrifuge is not entirely satisfactory. The amount of water detected is almost always lower than the actual water content. Therefore, when a high accurate value is required, another method must be used. This method also requires hazardous solvents and has very poor accuracy and reproducibility.

(Please see *Manual of Petroleum Measurement Standards*, Chapter 10.3—*Standard Test Method for Water and Sediment in Crude Oil by the Centrifuge Method* (*Laboratory Procedure*) for the complete protocol, which is hereby incorporated by reference.)

Distillation Method

In the standard test for determining the water content by distillation, the sample is heated under reflux conditions with a water immiscible solvent that co-distills with the water in the sample. The condensed solvent and water are continuously separated in a trap wherein the water settles in the graduated section of the trap, and the solvent returns to the distillation flask. The amount of water can then be determined on a volume or a mass basis.

The precision of this method can be affected by water droplets adhering to surfaces in the apparatus and, therefore, not settling into the water trap to be measured. To minimize this problem, all apparatus must be chemically cleaned at least daily to remove surface films and debris that hinder the free drainage of water in the apparatus.

If the system forms azeotropes, as in a benzene and cyclohexane system, a different problem arises, —the azeotropic composition limits the separation, and for a better separation, this azeotrope must be bypassed in some way. At low to moderate pressure, with the assumption of ideal-gas model for the vapor phase, the vapor-liquid phase equilibrium (VLE) of many mixtures can be adequately described by the following Modified Raoult's Law:

$$y_i P = x_i \gamma_i P_i^{sat} \text{ for } i=1, \ldots, c$$

where
- $y_i$ = mole fraction of component i in vapor phase;
- $x_i$ = mole fraction of component i in liquid phase;
- $P$ = system pressure;
- $P^{sat}$ = vapor pressure of component i; and
- $\gamma_i$ = liquid-phase activity coefficient of component i.

When $\gamma_i = 1$, the mixture is said to be ideal, and the equation simplifies to Raoult's Law. Nonideal mixtures ($\gamma_i \neq 1$) can exhibit either positive ($\gamma_i > 1$) or negative deviations ($\gamma_i < 1$) from Raoult's Law. In many highly nonideal mixtures, these deviations become so large that the pressure-composition (P-x, y) and temperature-composition (T-x, y) phase diagrams exhibit a minimum or maximum azeotrope point. In the context of the T-x, y phase diagram, these points are called the minimum boiling azeotrope (where the boiling temperature of the azeotrope is less than that of the pure component) or maximum boiling azeotrope (the boiling temperature of the azeotrope is higher than that of the pure components). About 90% of the known azeotropes are of the minimum variety. At these minimum and maximum boiling azeotrope, the liquid phase and its equilibrium vapor phase have the same composition, i.e.:

$$x_i = y_i \text{ for } i=1, \ldots, c \quad (2)$$

Two main types of azeotropes exist, i.e. the homogeneous azeotrope, where a single liquid phase is in the equilibrium with a vapor phase; and the heterogeneous azeotropes, where the overall liquid composition, which forms two liquid phases, is identical to the vapor composition. Most methods of distilling azeotropes and low relative volatility mixtures rely on the addition of specially chosen chemicals to facilitate the separation.

The drawbacks to this method include, for example, the fact that it utilizes hazardous solvents and produces hazardous vapors. This method also takes 2 to 3 hours to complete, and as with most distillation techniques, the accuracy and precision of the results will depend upon the skill of the technician performing the distillation. This method also does not provide any information with regard to the amount of sedimentation in the sample.

(Please see *Manual of Petroleum Measurement Standards*, Chapter 10.2—*Standard Test Method for Water in Crude Oil Distillation* for the complete protocol, which is hereby incorporated by reference.)

Zeolite Molecular Sieves

Molecular sieves, as used in this specification, include any material that can effectively be used to sequester or restrain or retain molecules in a material, such as, but not limited to, water molecules in a non-aqueous liquid, whether by physical capture within a crystalline structure, absorptive properties, adsorption, hydrogen bonding, or other means.

One class of molecular sieves includes crystalline, hydrated metal aluminosilicates. The commercially important types of molecular sieves are synthetically made, but their structure is similar enough to naturally occurring minerals to be classified as zeolites. Although the crystal structures of some of the molecular sieves are quite different, their absorbent property derives from their crystalline structure.

The crystalline metal aluminosilicate molecular sieves have a simple polyhedra arrangement. Each polyhedron is a three-dimensional array of $(Si, AlO_4)$ tetrahedral. The tetrahedra are formed by four oxygen atoms surrounding a silicon or aluminum atom. Each oxygen atom has two negative charges, and each silicon atom has four positive charges. This structure permits a net sharing arrangement, building a tetrahedron uniformly in four directions. The trivalency of aluminum causes the alumina tetrahedron to be negatively charged, requiring an additional cation to balance the system. Thus, the final structure has sodium, potassium, or calcium cations in the network. These "charge balancing" cations are the exchangeable ions of the zeolite structure.

Zeolites, one class of molecular sieves, exhibit electrical conductivity of an ionic type due to the migration of cations through the channel structure. The ability of the cations to carry a current depends upon their ionic mobility, charge, size, and location in the structure. The addition of water molecules to a dehydrated zeolite structure produces a pronounced change in the electrical conductivity of the zeolite. The conductivity of the zeolite increases with the amount of water present. The activation energy for conduction decreases with increasing adsorption of water. The influence of water is different for different zeolites. In some cases, the activation energy for conduction in a zeolite containing divalent ions is approximately twice that of a zeolite containing univalent ions.

When formed, this crystalline network is full of water, but with moderate heating, the moisture can be driven from the cavities without changing the crystalline structure—leaving countless cavities with their tremendous combined surface area and pore volume available for the adsorption of water or other materials.

With their large surface area and pore volume, molecular sieves then can perform virtually all the adsorption duties presently carried out by other absorbents. In addition, molecular sieves allow for a new dimension in process control because the pores of the crystalline network are uniform rather varied. Therefore, molecular sieves are able to differentiate molecules on the basis of molecular size and configuration.

Hence, molecular sieves utilize two adsorption mechanisms. They exhibit the capillary condensation phenomenon as a result of their large surface area and pore volume, and their polar surfaces have an electrostatic attraction for polar molecules such as water. This allows molecular sieves to be stronger absorbents than silica gel or alumina.

Another advantage to molecular sieves is that they can be packaged in foil-sealed bags to prevent moisture adsorption.

This allows them to have long term stability and makes them easy to use. Also, the measured quantity of molecular sieves can be accurately controlled.

Although this application refers to the adsorptive properties and activities of molecular sieves, it understood that a certain amount of absorption also takes place. Therefore, for the sake of simplicity, references to the adsorptive properties and activities of molecular sieves are intended to include any absorptive properties and activities as well.

The "Load-Pulled" Effect

It is well known to electrical engineers generally (and particularly to microwave engineers) that the frequency of an RF (radio frequency) oscillator can be "pulled" (i.e. shifted from the frequency of oscillation that would be seen if the oscillator were coupled to an ideal impedance-matched pure resistance) if the oscillator sees an impedance that is different from the ideal matched impedance. Thus, a varying load impedance may cause the oscillator frequency to shift.

The present application sets forth various innovative methods and systems that take advantage of this effect. In one class of embodiments, an unbuffered RF oscillator is loaded by an electromagnetic propagation structure that is electromagnetically coupled, by proximity, to a material for which real time monitoring is desired. The net complex impedance seen by the oscillator will vary as the characteristics of the material in the electromagnetic propagation structure vary. As this complex impedance changes, the oscillator frequency will vary. Thus, the frequency variation (which can easily be measured) can reflect changes in density (due to bonding changes, addition of additional molecular chains, etc.), ionic content, dielectric constant, or microwave loss characteristics of the medium under study. These changes will "pull" the resonant frequency of the oscillator system. Changes in the medium's magnetic permeability will also tend to cause a frequency change since the propagation of the RF energy is an electromagnetic process that is coupled to both electric fields and magnetic fields within the transmission line.

For further background and information on load-pulled systems, the reader is referred to U.S. Pat. No. 6,630,833 to Scott, which is hereby incorporated by reference.

Other Approaches to Electrical Characterization

Various types of apparatus have been proposed for measuring the concentration of one substance in another, particularly the concentration of a liquid or flowable substance in another liquid or flowable substance. Various devices that utilize the broad concept of determining composition of matter by measuring changes in a microwave signal are disclosed in U.S. Pat. Nos. 3,498,112 to Howard; 3,693,079 to Walker; 4,206,399 to Fitzky et al.; 4,311,957 to Hewitt et al.; 4,361,801 to Meyer et al.; 4,240,028 to Davis Jr.; 4,352,288 to Paap et al.; 4,499,418 to Helms et al.; and 4,367,440 and 4,429,273, both to Mazzagatti; all of which are hereby incorporated by reference.

Although various systems utilizing microwave transmissivity or signal alteration characteristics have been proposed in the prior art, certain considerations in utilizing microwave energy to detect the presence of the concentration of one medium in another have not been met by prior art apparatus. In particular, it is desirable in certain instances to be able to accurately measure, on a continuous basis, the concentration or change in concentration of one fluid in another and particularly where the concentration of one fluid is a very low percentage of the total fluid flow rate or fluid mixture quantity. It is also desirable that the signal change caused by the presence of one substance or medium in another be easily measured and be relatively error free, again, particularly in instances where measurements of low concentrations of one substance such as a fluid in another substance such as another fluid are being taken. Moreover, it is important to be able to transmit the microwave signal through a true cross section of the composition being sampled or measured to enhance the accuracy of the measurement.

Typical systems for capacitive-based measurement have a capacitive element, used for parameter determination, as part of the resonant feedback loop around an active device. This method works well with very low-loss systems, but oscillation ceases with even slightly lossy measurements. As the frequency is increased into the microwave region, it becomes difficult to configure the resonant feedback loop due to the increase in loss versus frequency and the wavelength becoming comparable to the path length. In this case, the frequency is changed directly by the resonance change in the feedback loop, which includes the element that consists of the sample to be measured. This frequency change is limited to the characteristics and loss of the feedback path and can only be changed over a narrow frequency range with out cessation of oscillations. This limits the measurement technique to small samples of very low loss.

At higher frequencies (above approximately 100 MHz), the capacitive measurement technique fails to work, due to line lengths and stray capacitances. At such frequencies, resonant cavity techniques have been employed. (For example, a sample is placed in a resonant cavity to measure the loss and frequency shift with an external microwave frequency source that can be swept across the resonance with and without the sample in the cavity.) This method uses a highly isolated microwave frequency source that is forced by the user (rather than being pulled by the changing resonance) to change its frequency. This technique too meets substantial difficulties. For example, the use of multiple interfaces without a microwave impedance match at each interface causes extraneous reflections, which tend to hide the desired measurement data. This technique too gives errors with very lossy material, but in this case, it is due to the very rounded nature of the resonance curve (which is due to the low Q of the loaded cavity). This rounded curve makes it difficult to determine both the center frequency and the 3 dB rolloff frequency closely enough to be accurate in the measurement.

Another technique that is used encompasses the use of a very sharp rise time pulse to obtain time domain data from which frequency domain values are then derived through transformation techniques.

In U.S. Pat. No. 4,396,062 to Iskander, entitled "Apparatus and Method for Time-Domain Tracking of High-speed Chemical Reactions", the technique used is time domain reflectometry (TDR). This contains a feedback system comprising a measurement of the complex permittivity by TDR means which then forces a change in frequency of the source, which is heating the formation to optimize this operation. Additionally, it covers the measurement of the complex permittivity by TDR methods.

U.S. Pat. No. 3,965,416 to Friedman appears to teach the use of pulse drivers to excite unstable, bi-stable, or relaxation circuits, and thereby propagate a pulsed signal down a transmission line that contains the medium of interest. The pulse delay is indicative of the dielectric constant of the medium. As in all cases, these are either square wave pulses about zero or positive or negative pulses. The circuit is a pulse delay oscillator where the frequency determining element is a shorted transmission line. The frequency generated is promoted and sustained by the return reflection of each pulse. The circuit will not sustain itself into a load that is lossy since the re-triggering will not occur without a return signal of sufficient magnitude. In addition, the circuit requires a load that is a DC short in order to complete the DC return path that is required for re-triggering the tunnel diodes.

The frequencies of operation of any pulse system can be represented as a Fourier Series with a maximum frequency that is inversely dependent upon the rise time of the pulse. Therefore, the system covered in the Friedman patent is dependent upon the summation of the frequency response across a wide bandwidth. This causes increased distortion of the return pulse and prevents a selective identification of the dielectric constant versus frequency. This also forces a design of the transmission system to meet stringent criteria to prevent additional reflections across a large bandwidth.

The low frequency limit of the TDR technique is determined by the time window, which is a function of the length of the transmission line. The upper extreme is determined by the frequency content of the applied pulse. In the case of this pulse delay line oscillator, the upper frequency is determined to a greater extent by the quality of impedance match (the lack of extra reflections) from the circuit through to the substance under study. These extra reflections would more easily upset the re-triggering at higher frequencies.

In one case (FIG. 1 of Friedman), the return reflection initiates a new pulse from the tunnel diode and, therefore, sets up a frequency (pulse repetition rate) as new pulses continue to be propagated. This is in essence a monostable multivibrator with the return reflection being the trigger. The problem implied, but not completely covered with this approach, is that due to the delay in pulses, the pulse train can overlap and cause multiple triggers to occur. These are caused by the re-reflections of the original parent pulse. An additional problem is with very lossy dielectrics, which will not provide enough feedback signal to initiate the next pulse. If the dielectric medium is of high enough dielectric constant to contain more than one wavelength, or if the dielectric constant of the samples vary greatly, multiple return reflections will alter the behavior of the circuit to render it useless due to the interfering train of return and parent pulses.

FIG. 3 of Friedman shows a bistable multivibrator that senses the return pulse by sampling and feeding back enough phase-shifted voltage to re-set the tunnel diodes. Since this device is also dependent upon the return to trigger or re-trigger the parent pulse, it suffers problems with lossy dielectrics and high dielectric constant mediums.

To overcome these problems, the relaxation oscillator of FIG. 4 of Friedman was proposed that contains a RC (resistor/capacitor timing) network that will maintain the generation of pulse trains using resistor 76 and capacitor 78 with the dielectric-filled transmission line affecting the regeneration of the pulses as the reflected parent pulse voltage is returned. Since the RC time constant is defining the basic repetition rate, some improvement is obtained in reducing second order effects. The transmission line is still an integral part of the overall relaxation oscillator, and lossy dielectrics may cause irregular circuit response. The proposed inverting amplifier as the pulse generator will not function at above approximately 1 MHz in frequency due to the characteristics of such inverting amplifiers. The tunnel diode can pulse up to a 100 MHz rate.

By contrast, the innovative system embodiments disclosed in the present application and its parents differ from the known prior art in using a microwave frequency generated by a free-running sine wave oscillator. The preferred oscillator has the versatile capability to work into a wide variety of transmission lines or other load impedance without generation of spurious data or cessation of oscillations. It will continue to oscillate with very lossy dielectrics. It is not a relaxation oscillator or a multivibrator. The frequency of the un-isolated oscillator is dependent upon the net complex impedance of the transmission line and will work into an open circuit as well as a short circuit. The net complex impedance at the frequency of operation of the oscillator looking at the transmission line containing the medium of interest results in stable oscillations through pulling of the unisolated oscillator. Only one frequency at any one time is involved in the disclosed system proposed (not counting harmonics that are at least 10 dB down from the fundamental). This provides for well-defined information and eases the transmission design criteria. This also provides for evaluation of the dielectric constant versus frequency that can improve resolution of constituents or ionic activity.

Another important difference from prior art is the separation of the load of interest from the resonant circuit proper. The configuration used isolates the two through the transistor. It is the non-linear behavior of the transistor that provides the changes in frequency as the load is changed. The loop gain of an oscillator must be unity with 180° phase shift. The initial gain of the transistor must be greater before oscillations begin in order for the oscillator to be self starting. This extra gain is reduced to unity by the saturation of the active device upon establishment of the oscillatory frequency. Saturating a device changes the gain (and accordingly the phase since it is non-linear) to maintain oscillations as the load changes. This will continue as the load changes as long as the transistor has appropriate phase and available gain to satisfy oscillations.

Aluminum Oxide for Moisture Adsorption

The use of aluminum oxide for moisture adsorption is well known in the industry. The surface attracts and retains water molecules by association with the bonds. Since this is a weak attraction, there is a point at which the absorption and desorption reaches an equilibrium with the surrounding moisture content. Moisture measurements have been made with capacitance measurements using a very thin aluminum oxide surface with imbedded electrodes. When the water is absorbed, the capacitance changes, and therefore, a measurement is made. This surface must be thin in order to allow the water molecules to accumulate in a region where the electrical field is present.

Moisture and Sediment Analysis

The present inventions describe systems and methods for the determination of the water and sediment content in a petroleum sample.

The present innovations include, in one embodiment, collecting a sample to be tested in a field bottle. The sample from the field bottle is then transferred from the field bottle, and into and through an analysis bottle containing a desiccant material. As the sample is being pulled through the analysis bottle, a microwave measurement system (or other scattering parameter measuring system) is used to measure the effects of the sample on the scattering parameters of the desiccant material. By measuring the effects of the sample on the scattering parameters of the desiccant material, the sample's moisture content can be determined. The sample's moisture can also be determined by measuring the expanded volume of the desiccant. A filter section having a sight glass with graduations is used to determine the sediment content of the sample.

Hence, the disclosed innovations provide a simple approach to measuring the moisture and sediment content in crude oil that is extremely fast, accurate, and reproducible without the use of hazardous chemicals. Other embodiments are described more fully below.

BRIEF DESCRIPTION OF THE DRAWINGS

The disclosed inventions will be described with reference to the accompanying drawings, which show important sample embodiments of the invention and which are incorporated in the specification hereof by reference, wherein:

FIGS. 10A and 10B show general block diagrams of the load-pulled method and the phase/amplitude measuring microwave method utilized by the present inventions.

DETAILED DESCRIPTION OF THE PREFERRED EMBODIMENTS

The numerous innovative teachings of the present application will be described with particular reference to the presently preferred embodiments (by way of example, and not of limitation).

In one embodiment, the present innovations involve obtaining a sample of petroleum for moisture and sediment determination in a field bottle, and placing the sample-filled field bottle in an apparatus that punctures the field bottle allowing the sample to flow from the field bottle and into an analysis bottle containing a desiccant material. A pump or vacuum pulls the sample through the analysis bottle. As the sample is being pulled through the analysis bottle, a microwave measurement system (or other scattering parameter measuring system) is used to measure the effects of the sample on the scattering parameters of the desiccant material. By measuring the effects of the sample on the scattering parameters of the desiccant material, the sample's moisture content can be determined. The sample's moisture can also be determined by measuring the expanded volume of the desiccant. A filter section having a sight glass with graduations is used to determine the sediment content of the sample.

In one embodiment, the microwave system measures phase and amplitude via scattering parameters of the system. In another embodiment, the microwave system is a load-pulled microwave system.

Although both systems measure the parameters of the microwave propagation parameters, they determine the moisture content by different means. Specifically, a non-load pulled microwave system measures the amplitude phase of the waves, such as reflections, transmission losses, and phase angles. These measurements are used to determine the change in scattering parameters. This change would then be compared to a previously generated calibration to then output by screen, digital, or analog the moisture content of the sample. By contrast, a load-pulled microwave system uses the changes in the frequency readings of the scattering parameters of the desiccant material as the sample is being pulled through it to determine the moisture content of the sample.

Both methods take less than a few seconds to determine the moisture content.

Once the moisture and sediment content of the sample has been determined, the analysis bottle would be removed leaving the microwave portion clean and free for the next analysis.

Figure 1A:
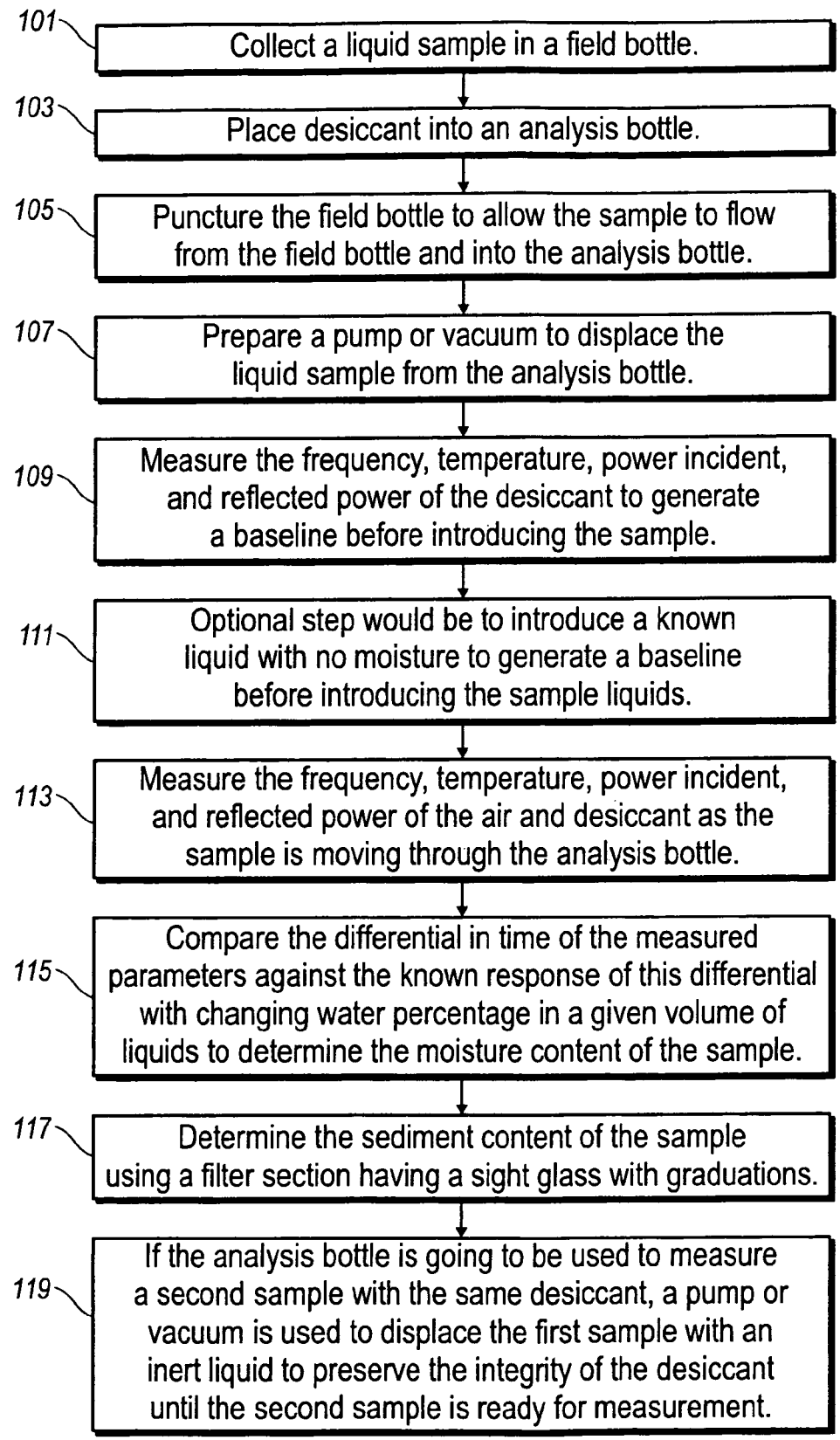
FIGS. 1A and 1B are flow charts of preferred embodiments of the present inventions.

FIG. 1A is a flow chart of a preferred embodiment of the present inventions. In this embodiment, a liquid sample is collected in a field bottle (step 101). A desiccant material is placed into an analysis bottle (step 103). An apparatus is used to puncture the field bottle allowing the sample to flow from the field bottle and into the analysis bottle containing a desiccant material (step 105). A pump or vacuum is then prepared to displace the liquid sample from the analysis bottle (step 107). Alternatively, the sample need not be passed though, for example when measuring a static sample. In one embodiment, the frequency, temperature, power incident, and reflected power of the desiccant material are measured to generate a baseline before introducing the sample liquids (step 109). In another embodiment, an optional step would be to introduce a known liquid with no moisture to generate a baseline before introducing the sample liquids (step 111). The frequency, temperature, power incident, and reflected power of the air and desiccant material are measured as the sample is moving through the analysis bottle (step 113). The differential in time of the measured parameters is compared against the known response of this differential with changing water percentage in a given volume of liquids (step 115) to determine the moisture content of the sample. A filter section having a sight glass with graduations is used to determine the sediment content of the sample (step 117). If the analysis bottle is going to be used to measure a second sample with the same desiccant material, a pump or vacuum is used to displace the first sample with an inert liquid to preserve the integrity of the desiccant material until the second sample is ready for measurement (step 119).

Figure 1B:
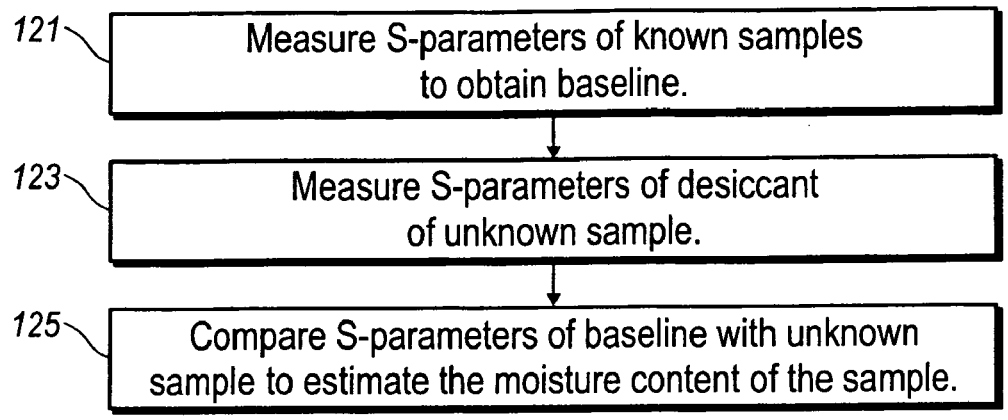

FIG. 1B shows a flowchart consistent with implementing a preferred embodiment of the present invention. This flowchart provides a broad overview of the present innovations. First, s-parameters of a known sample are measured using a microwave oscillator system to obtain baseline curves (step 121). In this step, materials with known water content, for example, in oil are measured, and their effects on s-parameters are determined. By generating several such curves, liquids with unknown quantities can be measured (step 123), and the results compared with the baseline graphs to estimate, for example, the water content of the sample (step 125). It is noted that the content of water in oil is only one example of what can be tested.

Figure 2:
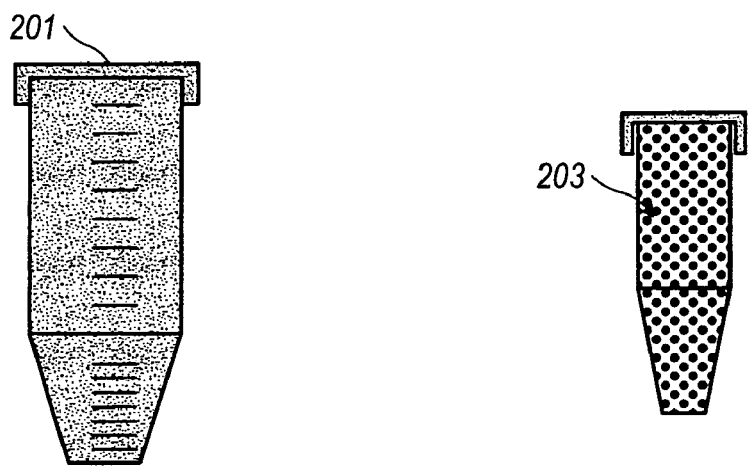
FIG. 2 shows a field bottle and an analysis bottle with a desiccant material.

FIG. 2 shows a sample embodiment of a field bottle 201 and an analysis bottle 203. Both bottles can be standard plastic centrifuge tubes such as Cole-Palmer A-06334-40 and A-17410-20 with lids. In this particular embodiment, field bottle 201 is a 250 ml. container used by field personnel to pull a sample from a crude oil pipeline. Analysis bottle 203 is used to determine the water content of the sample in field bottle 201. Analysis bottle 203 is a 50 ml. container prepared with molecular sieves or similar desiccant. The molecular sieves or desiccant material can be in the form of powder, balls, rods, or chips that are contained within the bottle by an internal cap. Analysis bottle 203 is then sealed with a lid and may be placed in a vacuum foil package to preserve the dryness of the desiccant.

Figure 3A:
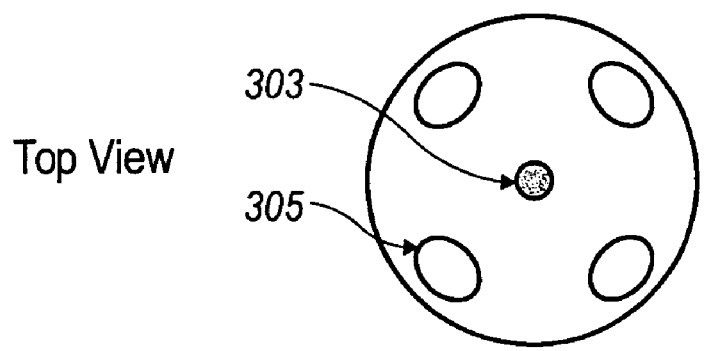
FIG. 3 shows the top view and the side view of a sample embodiment of a cup designed to seal onto the top of an analysis bottle.
Figure 3B:
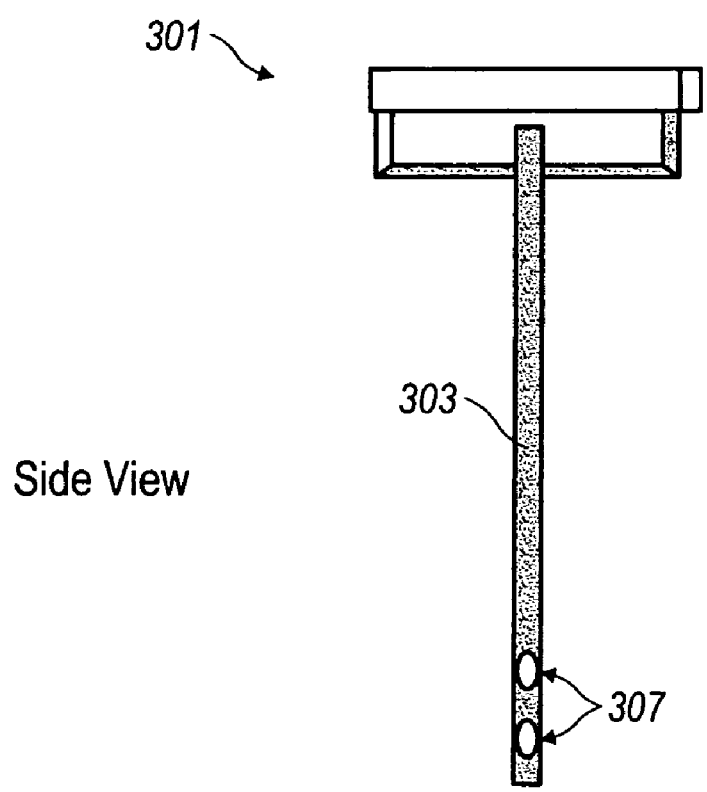

FIG. 3 shows the top view and the side view of a sample embodiment of a cup 301 designed to seal onto the top of an analysis bottle. The top view shows a center tube 303 for pulling the sample through the system and multiple holes 305 to allow a sample to enter the analysis bottle from an upper field bottle. The side view shows holes 307 at the end of center tube 303. Holes 307 serve to pull a sample through the system.

Figure 4:
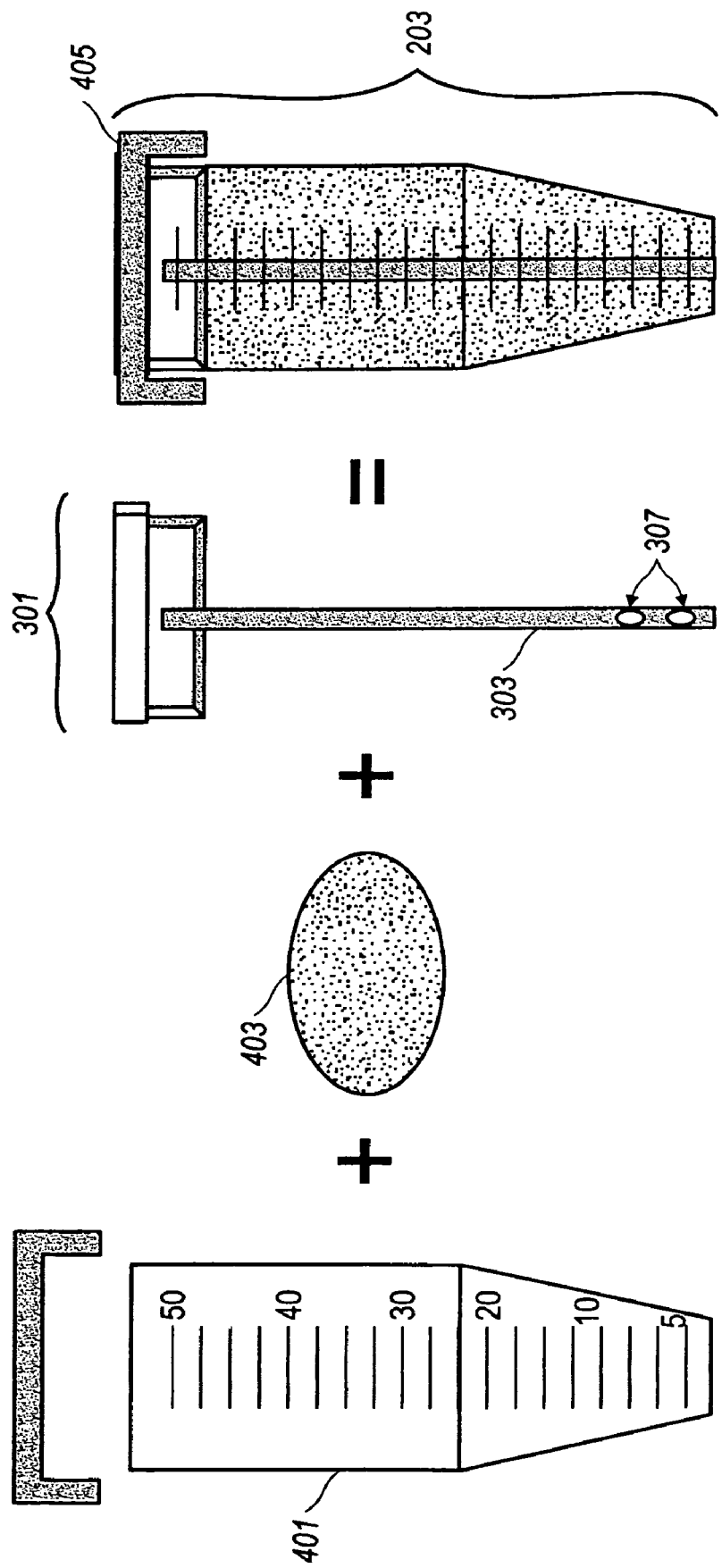
FIG. 4 shows a general layout of a sample embodiment of an analysis bottle.

FIG. 4 shows a general layout of a sample embodiment of an analysis bottle. In this embodiment, analysis bottle 203 is formed by a graduated centrifuge tube 401. Centrifuge tube 401 is filled with desiccant material 403. Cup 301 is then placed inside centrifuge tube 401 to seal desiccant material 403 into analysis bottle 203. The desiccant material is chosen such that the desiccant material is larger than holes 307 at the end of center tube 303. A screw-on lid 405 is then used to seal the assembly. This assembly may be sealed in a vacuum-sealed foil wrapper to prevent moisture contamination.

Figure 5:
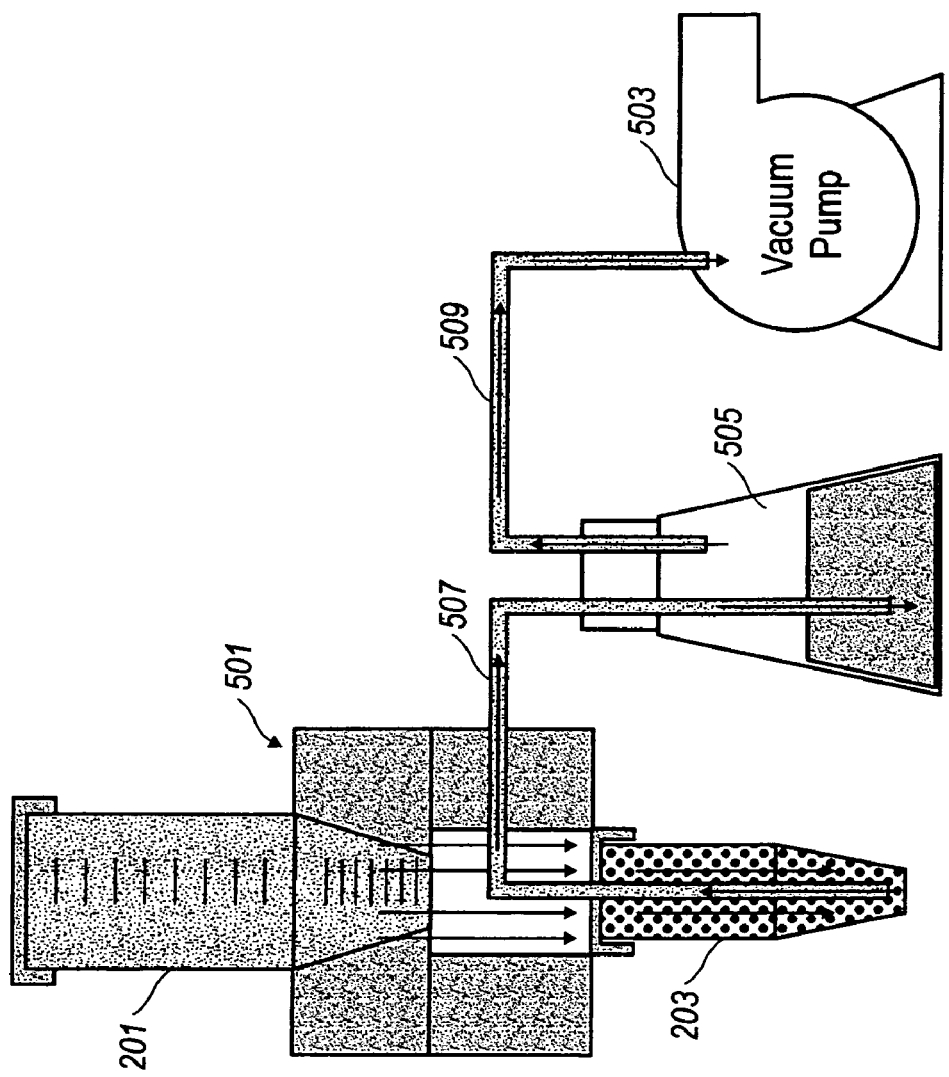
FIG. 5 shows a general layout of a sample embodiment in which a sample is pulled from a field bottle and through an analysis bottle by means of a vacuum source.

FIG. 5 shows a general layout of a sample embodiment of a system in which a sample is pulled from field bottle 201 and into and through analysis bottle 203. In this particular embodiment, apparatus 501 punctures the bottom of field bottle 201 and connects the lower analysis bottle 203 with the upper field bottle 201. Once a sample has entered analysis bottle 203 from punctured field bottle 201, a vacuum source 503 is used to purge the sample into flask 505 via ports 507 and 509. This avoids contamination of the next sample, as well as minimizes disposal. Although this figure shows the sample purged into a flask, the sample may also be blown back into the main tank.

Figure 6:
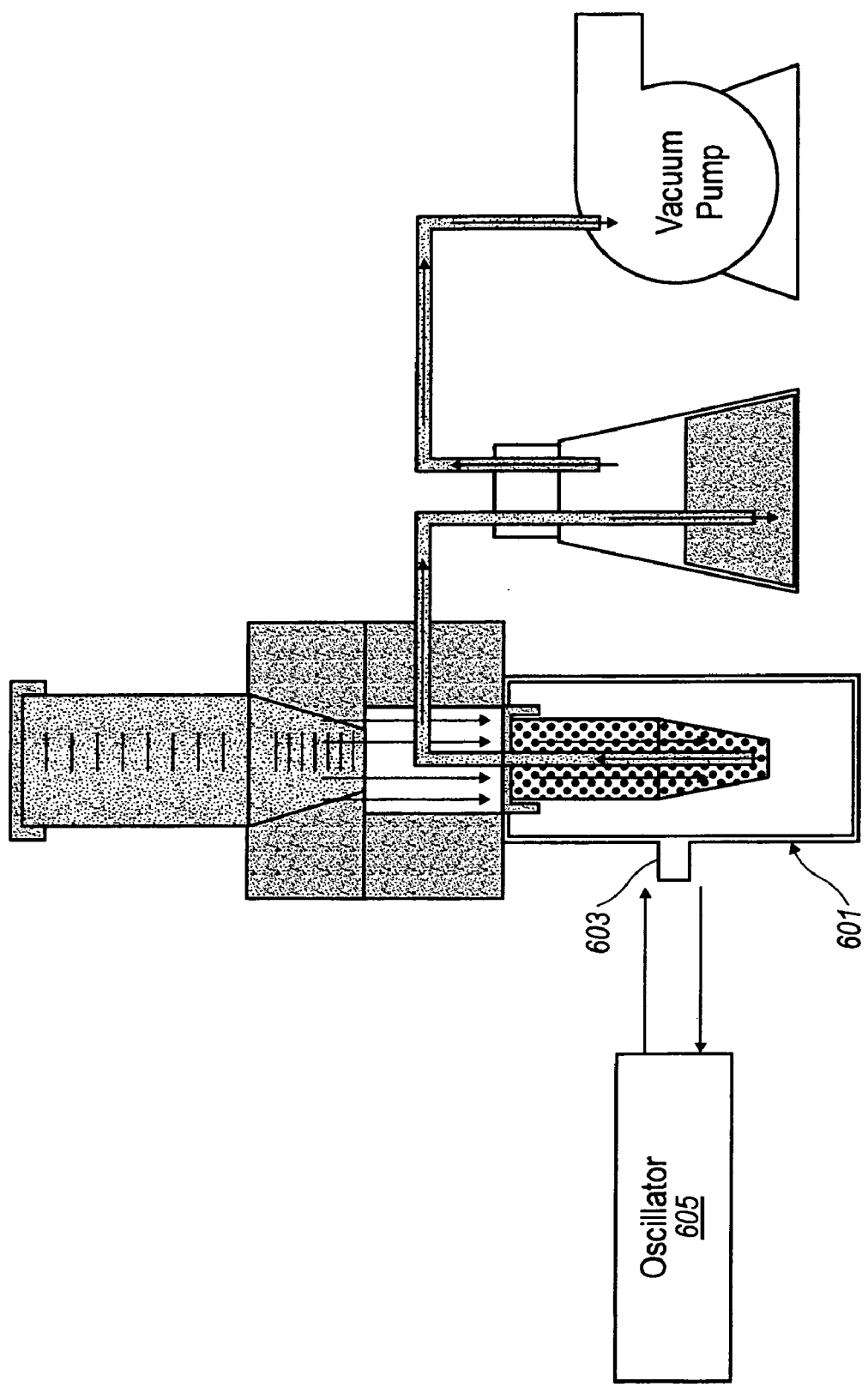
FIG. 6 shows a general layout of a sample embodiment in which the analysis bottle is inside a microwave cavity.

FIG. 6 shows another general layout of the system shown in FIG. 5. In this embodiment, analysis bottle 203 is inside a microwave cavity 601 that measures the change in permittivity as moisture is captured by the desiccant. Microwave cavity 601 is shown with a microwave measurement port 603 coupled to an oscillator 605.

Microwave cavity 601 can be coaxial such that the center conductor can be imbedded into analysis bottle 203. In this case, a metal center pipe would be used to provide a contact on the bottom of analysis bottle 203.

Microwave cavity 601 can also be waveguide such that analysis bottle 203 is placed directly inside a cavity that is shaped like analysis bottle 203. In this case, ceramic beads or similar material to the desiccant may need to be placed between the electromagnetic launch point to maintain cavity integrity by preventing reflections from affecting the measurement. Also, waveguide dimensions will be altered by the presence of the desiccant. Therefore, the cut off frequency will be lower and will need to be accounted for at the launch point of the electromagnetic energy into the waveguide.

Figure 7:
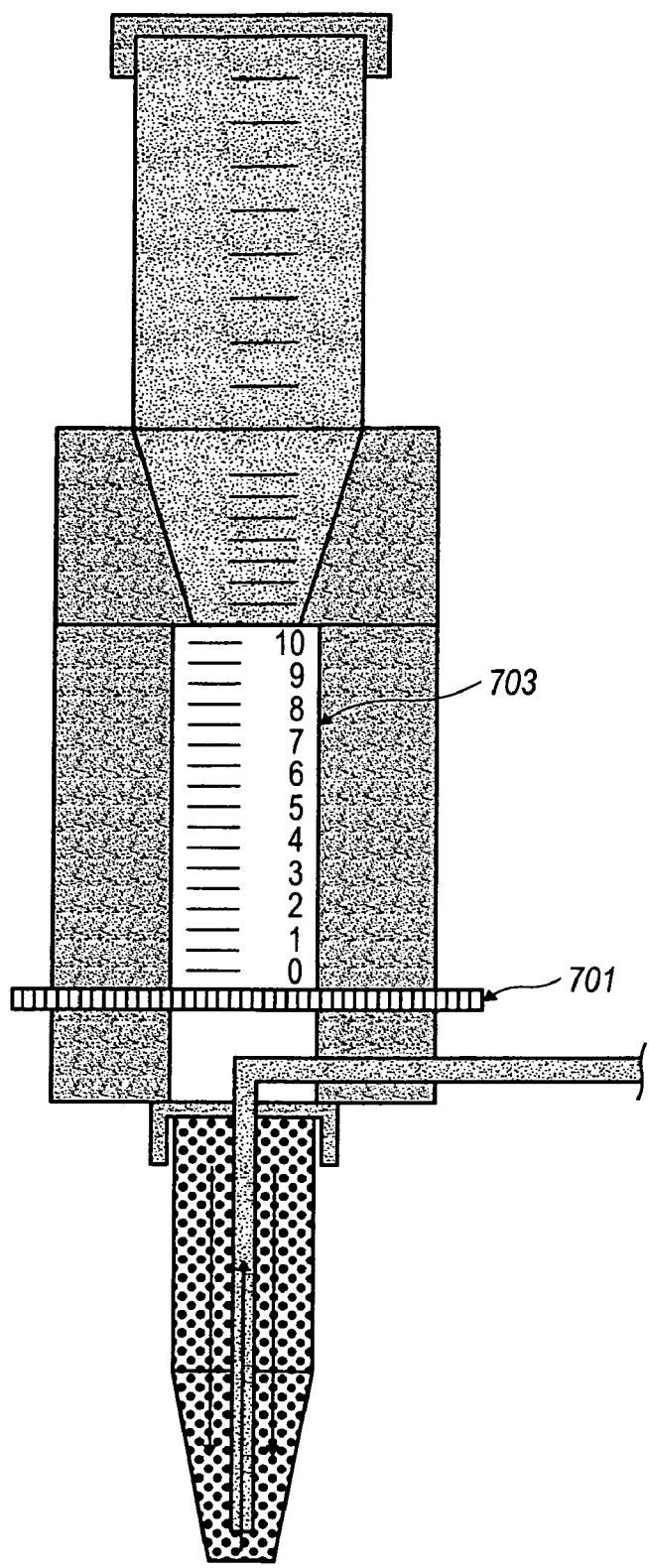
FIG. 7 shows a general layout of a sample embodiment utilizing a sediment filter with a sight glass tube.

FIG. 7 shows another general layout of the systems shown in FIGS. 5 and 6 utilizing a sediment filter with a sight glass tube. In this particular embodiment, fixture 501 has a filter 701 that prevents sediments from the sample in field bottle 201 from entering or settling on top of analysis bottle 203. A sight glass tube 703 with graduations is used to measure the sediment content of the sample.

Figure 8:
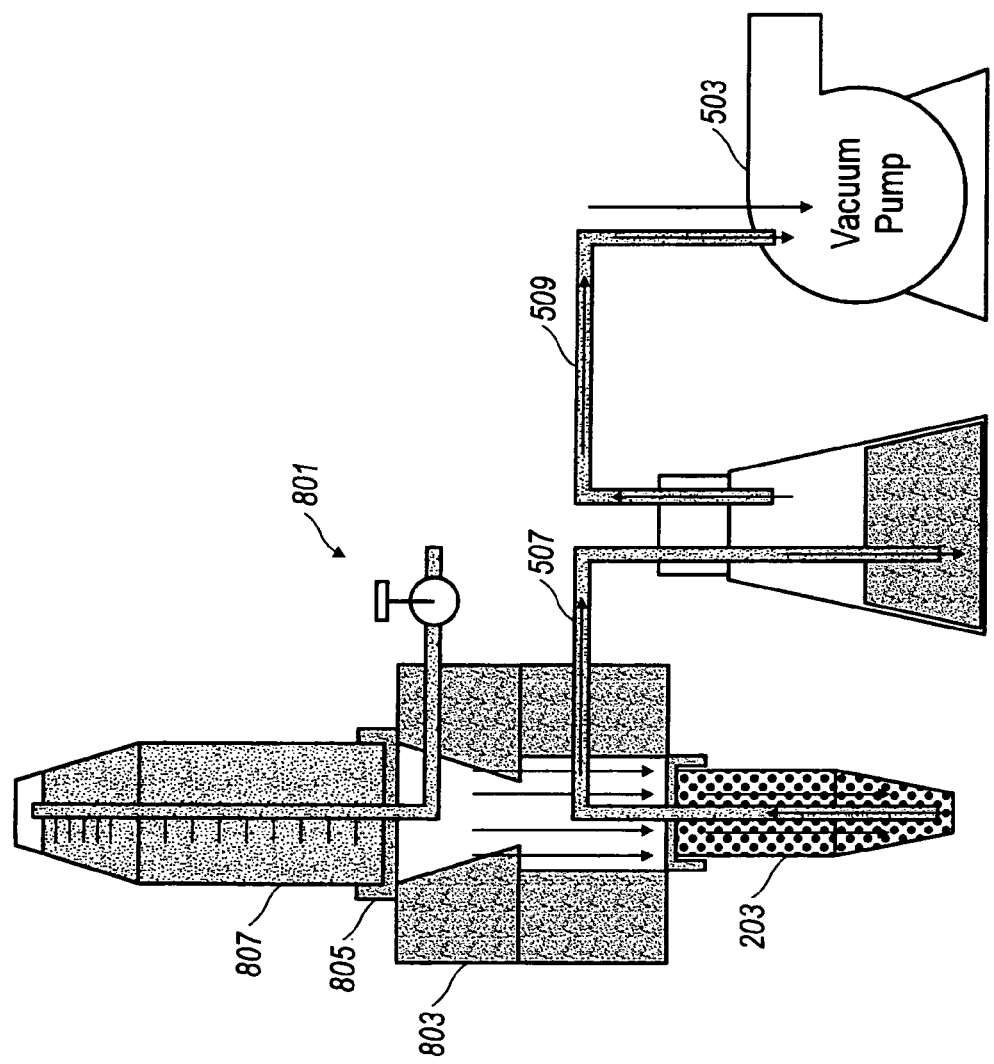
FIG. 8 shows a general layout of a sample embodiment of a system that utilizes a valve system to bleed air into the field bottle to allow the sample the flow through the system.

FIG. 8 shows a general layout of a sample embodiment of a system that utilizes a valve system to bleed air into the field bottle to allow the sample the flow through the system. In this particular embodiment, valve system 801 is formed into apparatus 803 and lid 805 of field bottle 807. Apparatus 803 connects lower analysis bottle 203 with the upper field bottle 807. Once a sample has entered analysis bottle 203 from field bottle 807, vacuum source 503 is used to purge the sample into flask 505 via ports 507 and 509.

Figure 9:
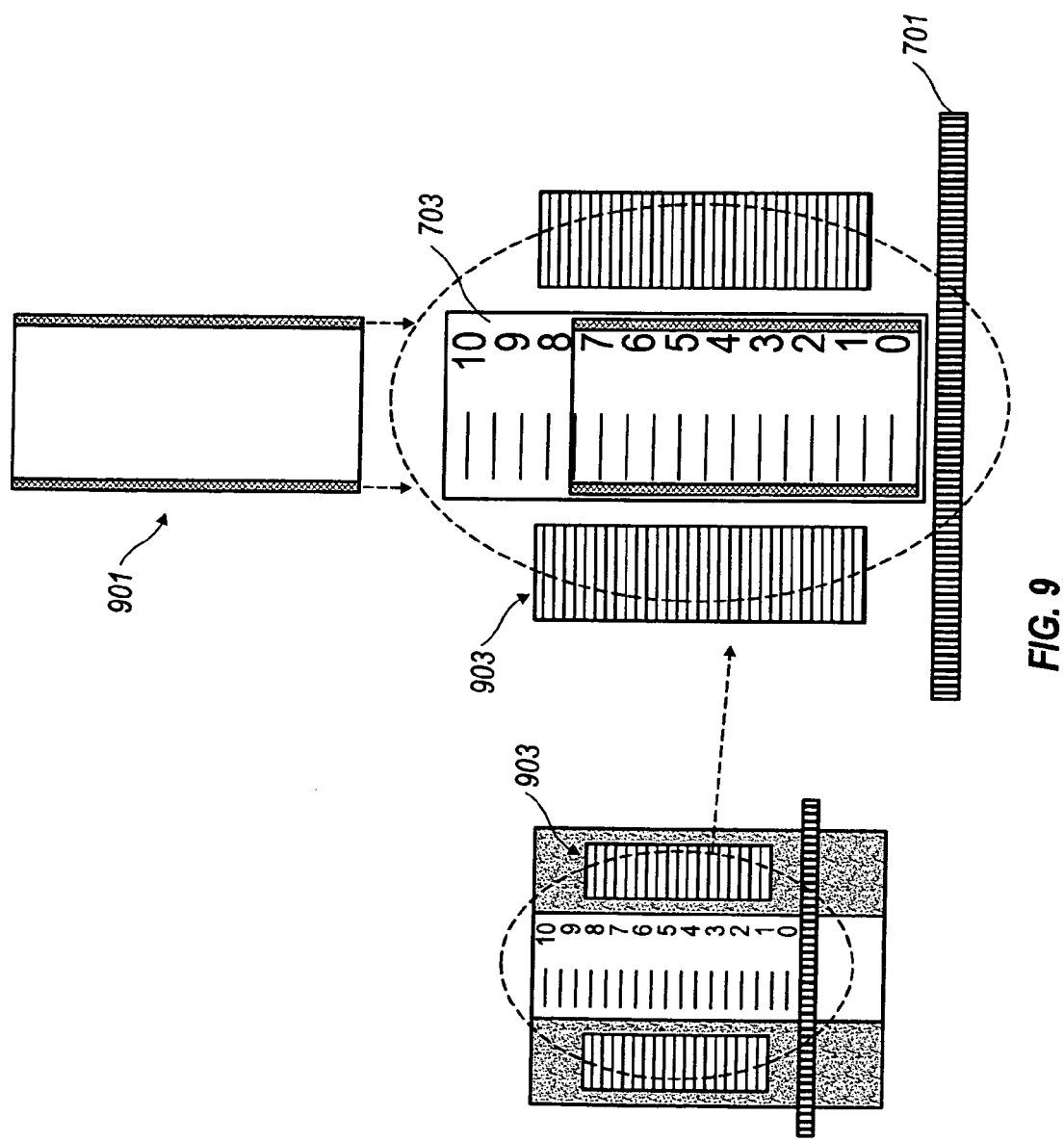
FIG. 9 depicts another general layout of sight glass tube.

FIG. 9 depicts another general layout of sight glass tube 703. In this particular embodiment, a cylindrical, magnetic-coupled stirrer 901 is placed inside sight glass tube 703. Stirrer 901 forms a rotor to rotate the sample. This helps to prevent sediments from clogging filter 701. Magnetic coils 903 are pulsed in sequence to rotate the magnetic poles in the stirrer. Stirrer 901 can be, for example, a Teflon-coated, powder magnetic structure.

FIG. 10A shows general block diagrams of the load-pulled method, consistent with implementing a preferred embodiment of the present invention. With the load-pulled method, a cavity 1001 is first loaded with the molecular sieves and the sample. A microwave oscillator 1003 then propagates microwaves through the molecular sieves. A frequency counter 1005 detects the frequency of the oscillator and measurement system with the molecular sieve. Additionally, the incident and reflected power could be a measured parameter. A microprocessor 1007 then generates a moisture content reading 1009 from the frequency readings from frequency counter 1005.

FIG. 10B shows a microwave system equipped for measuring phase and amplitude of the incident and reflected waves, for example. Microwave oscillator 1011 transmits microwaves to a power splitter 1013. Power splitter 1013 then outputs an incident power measurement 1015 to microprocessor 1017. Power splitter 1013 also delivers a second output signal to directional coupler 1019. Directional coupler 1019 couples the signal from power splitter 1013 with the signal from cavity 1021, which is loaded with molecular sieves and sample, to generate a reflected power and phase measurement 1023 for microprocessor 1017. The signal from cavity 1021 is then used to generate a transmitted power measurement 1025 for microprocessor 1017. Microprocessor 1017 then compares these measurements to a previously generated calibration to generate a moisture content reading 1027 for the sample.

Since molecular sieves vary in methods of water absorption, size, and packing density, methods applicable to the particular type of sieve will be adapted to provide reproducible results. For example, the heat of absorption can be large, and therefore, a temperature measurement and correction may be needed. The packing density of the molecular sieve may require selection of a specific geometry of the molecular sieve (i.e. round, square, rectangle, etc.) to achieve reproducibility and ease of handling.

In the present innovations, the reaction being used is preferably a non-equilibrium reaction. Therefore, in preferred embodiments, it is irreversible and will run to completion if allowed. This is in contrast to an equilibrium reaction, which is a reversible reaction and actually involves two reactions. There is a "forward" reaction and a mirror image "reverse" reaction. The reactants combine to form products. The products "decompose" to form reactants. Therefore, it is not necessary to determine whether the reaction has reached equilibrium or if certain factors, such as changes in the temperature or pressure, have unknowingly caused the equilibrium point to shift. Characterizing a non-equilibrium reaction eliminates these concerns.

However, the molecular sieves themselves would initially start with a mass transfer zone (MTZ) in the initial area where it first comes into contact with the sample. As time progresses, this mass transport zone continuously moves away from this initial area. Hence, upstream of the MTZ, the molecular sieves have reached equilibrium with the sample, while downstream of the MTZ, the molecular sieves are still in equilibrium with the air in the system.

A very important advantage of the disclosed innovations is that they provide a measurement technique that is suitable for field use.

Another important advantage of the disclosed innovations is that they provide a measurement technique that is suitable for use by relatively untrained personnel. With sample conditions and additives standardized as described herein, the sampling technician can be allowed to use the measurement unit simply as a black box.

Another important advantage is that the testing of the analysis bottles is nondestructive. Thus, some fraction of sample bottles can be systematically retained, if desired, for rechecking in case of later dispute.

Another important advantage is that the analysis bottles, once filled with the fluid being tested, do not have to be reopened. Thus, fluids, such as crude oil, which are environmentally undesirable can be properly disposed of simply by putting the filled bottles in appropriate disposal containers. Also, some desiccants, such as molecular sieves, are naturally occurring materials and are environmentally friendly.

In one important class of embodiments, bottles and desiccants as described above are used for field assay at the point where a tanker is being loaded or unloaded. This very simple assay-at-lading technique provides simple verification of crude oil assay, and hence reduced commercial disputes.

In another class of embodiments, standardized bottles as described above can be used for field sampling (e.g. at sample collection tap valves at dockside), and the electronic measurement can be done in a unit that is transportable, but not normally hand-carried. Thus, for example, a field auditor might fill a dozen labeled field bottles at various points in a pumping facility, and then return to the analyzer in his truck, which is calibrated as described above, to obtain moisture and sediment analysis for each.

According to a disclosed class of innovative embodiments, there is provided: A method for determining the water and sediment content of a fluid, comprising the steps of: collecting the fluid in a first bottle; transferring the fluid from the first bottle and into a second bottle, the second bottle containing an absorbent material; determining the water content of the fluid by measuring the expanded volume of the absorbent material; and determining the sediment content of the fluid by reading the sediment level from a filter section having a graduated sight glass.

According to a disclosed class of innovative embodiments, there is provided: A method of testing a sample, comprising the steps of: using an apparatus that detects change in scattering parameters to characterize one or more known materials to obtain one or more baselines; testing an unknown sample in the presence of a desiccant material to detect scattering parameters to obtain a result; comparing the result with the one or more baselines; wherein the desiccant material and sample are tested in a non-equilibrium process; and wherein a filter section with a graduated sight glass is used for estimating the sediment content of the sample.

According to a disclosed class of innovative embodiments, there is provided: A method for determining the moisture and sediment content of a fluid, comprising the steps of: collecting the fluid in a first bottle; transferring the fluid from the first bottle and into a second bottle, the second bottle containing a desiccant material; displacing the fluid from the second bottle; as the fluid flows into and is displaced from the second bottle, electrically characterizing the desiccant material and fluid, using an electrical measurement stage which is electromagnetically coupled thereto; and which outputs a test signal which is dependent on the permittivity of the desiccant material and fluid; and calculating and then outputting, from at least one stored calibration value for the electrical measurement stage and the desiccant material and the fluid, an indicated moisture content value; and determining the sediment content of the fluid by reading the sediment level from a filter section having a graduated sight glass.

According to a disclosed class of innovative embodiments, there is provided: A method for field-testing the moisture and sediment content in a non-aqueous fluid, comprising: a) collecting the fluid in a first bottle; b) transferring the fluid from the first bottle and into a second bottle, the second bottle containing an absorbent material; c) electrically characterizing the absorbent material after contact with the fluid, using an electrical measurement stage which is electromagnetically coupled thereto and which outputs a test signal which is dependent on the permittivity of the fluid; d) draining the fluid from the absorbent material; and e) at two or more iterations of steps a through d, calculating from at least one stored calibration value for the electrical measurement stage and the absorbent material and the fluid, a starting moisture loading value for the absorbent material, a resulting moisture loading value for the absorbent material, and f) calculating therefrom and then outputting an indicated moisture content value for the fluid; and g) determining the sediment content of the fluid by reading the sediment level from a filter section having a graduated sight glass.

According to a disclosed class of innovative embodiments, there is provided: A system for determining the water and sediment content of a sample, comprising: an apparatus for transferring a sample into and out of an analysis bottle, the apparatus having a filter section with a graduated sight glass; and the analysis bottle having an absorbent material; wherein the water content of the fluid is determined by measuring the expanded volume of the desiccant; and wherein the sediment content of the fluid is estimated by reading its level from the graduated sight glass of the filter section.

According to a disclosed class of innovative embodiments, there is provided: A system for characterizing a sample, comprising: an apparatus for transferring a sample to an analysis bottle, the analysis bottle having a desiccant material; an oscillator measurement system coupled to the analysis bottle; wherein the sample is characterized by a change in a property of a signal of the oscillator measurement system; wherein the oscillator measurement system is pre-calibrated for the analysis bottle and desiccant material; and wherein the apparatus also has a filter section with a graduated sight glass for estimating the sediment content of the sample.

According to a disclosed class of innovative embodiments, there is provided: A field-testing system for analysis of moisture and sediment content in non-aqueous samples, comprising: an apparatus for transferring a sample to an analysis bottle, the analysis bottle having a pre-measured quantity of an absorbent material; an electrical measurement stage which is electromagnetically coupled to the analysis bottle; which outputs a test signal which is dependent on the permittivity of the absorbent material; and which is pre-calibrated for the pre-measured quantity of the absorbent material; a calculation stage which looks up the output of the electrical measurement stage to obtain an indicated moisture content value; and a filter section with a graduated sight glass for estimating the sediment content of the sample.

According to a disclosed class of innovative embodiments, there is provided: A system for determining the moisture and sediment content of a fluid, comprising: a first bottle for collecting a fluid to be analyzed; a second bottle containing a desiccant material; a first apparatus for transferring the fluid from the first bottle to the second bottle, first apparatus having a filter section with a graduated sight glass; a second apparatus for displacing fluid from the second bottle; and an electrical measurement stage; wherein the electrical measurement stage is electromagnetically coupled to the second bottle; and outputs a test signal which is dependent on the permittivity of the desiccant material and fluid as the fluid flows into and is displaced from the second bottle; and calculates and then outputs, from at least one stored calibration value for the electrical measurement stage and the desiccant material and the fluid, an indicated moisture content value; and wherein the sediment content of the fluid is estimated by reading its level from the graduated sight glass of the filter section.

DEFINITIONS

Following are short definitions of the usual meanings of some of the technical terms which are used in the present application. (However, those of ordinary skill will recognize whether the context requires a different meaning.) Additional definitions can be found in the standard technical dictionaries and journals.

The term "molecular sieve" includes both synthetic and naturally occurring zeolites, as well as any other material that can effectively be used to sequester, restrain or retain molecules in a material, such as (but not limited to) water molecules in a non-aqueous liquid, whether by physical capture within a crystalline structure, absorption, adsorption, hydrogen bonding, or other means including wherein the sieve behaves as a reactant in bonding with a material.

A list of zeolytes is provided for purposes of inclusion, and is not intended to limit the number of materials capable of being implemented in the present invention as a molecular sieve material:

| Code | Abbreviated Name | Full name |
| --- | --- | --- |
| ABW | | Li-A (Barrer and White) |
| ACO | ACP-1 (one) | Aluminium Cobalt Phosphate-one |
| AEI | AlPO$_4$-18 (eighteen) | Aluminophosphate-eighteen |
| AEL | AlPO$_4$-11 (eleven) | Aluminophosphate-eleven |
| AEN | AlPO-EN3 | Aluminophosphate ethylenediamine (en)-3 |
| AET | AlPO$_4$-8 (eight) | Aluminophosphate-eight |
| AFI | AlPO$_4$-5 (five) | Aluminophosphate-five |
| AFO | AlPO$_4$-41 (forty-one) | Aluminophosphate-forty-one |
| AFR | SAPO-40 (forty) | Silico-Aluminophosphate-forty |
| AFS | MAPSO-46 (forty-six) | MgAl(P, Si)O$_4$-46 |
| AFT | AlPO$_4$-52 (fifty-two) | |
| AFX | SAPO-56 (fifty-six) | Silico-Aluminophosphate-fifty-six |
| AFY | CoAPO-50 (fifty) | |
| AHT | AlPO$_4$-H2 (two) | |
| APC | AlPO$_4$-C | |
| APD | AlPO$_4$-D | |
| AFN | AlPO$_4$-14 (fourteen) | |
| AST | AlPO$_4$-16 (sixteen) | |
| ATN | MAPO-39 (thirty-nine) | MgAlPO$_4$-thirty-nine |
| ATT | AlPO$_4$-12 (twelve)-TAMU | AlPO$_4$-12-Texas A&M University |
| ATV | AlPO$_4$-25 (twenty-five) | |
| AWO | AlPO$_4$-21 (twenty-one) | |
| AWW | AlPO$_4$-22 (twenty-two) | |
| BPH | | Beryllophosphate-Harvey (or hexagonal) |
| CGF | CoGaPO-5 (five) | Cobalt-Gallium-Phosphate-five |
| CGS | CoGaPO-6 (six) | Cobalt-Gallium-Phosphate-six |
| CON | CIT-1 (one) | California Institute of Technology-one |
| CFI | CIT-5 (five) | California Institute of Technology-five |
| CZP | | Chiral Zincophosphate |
| DDR | Deca-dodecasil 3R | Deca- & dodecahedra, 3 layers, rhombohedral |
| DFO | DAF-1 (one) | Davy Faraday Research Laboratory-one |
| DFT | DAF-2 (two) | Davy Faraday Research Laboratory-two |
| DOH | Dodecasil 1H | Dodecahedra, 1 layer, hexagonally stacked |
| DON | UTD-1 (one) | University of Texas at Dallas-one |
| EAB | | TMA-E (Aiello and Barrer) |
| EMT | EMC-2 (two) | Elf (or Ecole Supérieure) Mulhouse Chimie-two |
| ESV | ERS-7 (seven) | Eniricerche-molecular-sieve-seven |
| EUO | EU-1 (one) | Edinburgh Univerisity-one |
| IFR | ITQ-4 (four) | Instituto de Tecnologia Quimica Valencia-four |
| ISV | ITQ-7 (seven) | Instituto de Tecnologia Quimica Valencia-seven |
| ITE | ITQ-3 (three) | Instituto de Tecnologia Quimica Valencia-three |
| JBW | | NaJ (Barrer and White) |
| KFI | ZK-5 (five) | Zeolite Kerr-five |
| LOS | Losod | Low sodium aluminosilicate |
| LTA | Linde Type A | Zeolite A (Linde Division, Union Carbide) |
| LTL | Linde Type L | Zeolite L (Linde Division, Union Carbide) |
| LTN | Linde Type N | Zeolite N (Linde Division, Union Carbide) |
| MEI | ZSM-18 (eighteen) | Zeolite Socony Mobil-eighteen |
| MEL | ZSM-11 (eleven) | Zeolite Socony Mobil-eleven |
| MFI | ZSM-5 (five) | Zeolite Socony Mobil-five |
| MFS | ZSM-57 (fifty-seven) | Zeolite Socony Mobil-fifty-seven |
| MSO | MCM-61 (sixty-one) | Mobil Composition of Matter-sixty-one |
| MTN | ZSM-39 (thirty-nine) | Zeolite Socony Mobil-thirty-nine |
| MTT | ZSM-23 (twenty-three) | Zeolite Socony Mobil-twenty-three |
| MTW | ZSM-12 (twelve) | Zeolite Socony Mobil-twelve |
| NES | NU-87 (eighty-seven) | New (ICI)-eighty-seven |
| NON | Nonasil | Nonahedra, all silica composition |
| OSI | UiO-6 (six) | University of Oslo-six |
| RSN | RUB-17 (seventeen) | Ruhr University Bochum-seventeen |
| RTE | RUB-3 (three) | Ruhr University Bochum-three |
| RTH | RUB-13 (thirteen) | Ruhr University Bochum-thirteen |
| RUT | RUB-10 (ten) | Ruhr University Bochum-ten |
| SBE | UCSB-8 (eight) | University of California, Santa Barbara-eight |
| SBS | UCSB-6 (six) | University of California, Santa Barbara-six |
| SBT | UCSB-10 (ten) | University of California, Santa Barbara-ten |
| SAO | STA-1 (one) | Univeristy of Saint Andrews-one |
| SAT | STA-2 (two) | Univeristy of Saint Andrews-two |
| SGT | Sigma-2 (two) | |
| SFF | SSZ-44 (forty-four) | Standard Oil Synthetic Zeolite-fourty-four |
| STF | SSZ-35 (thirty-five) | Standard Oil Synthetic Zeolite-thirty-five |
| STT | SSZ-23 (twenty-three) | Standard Oil Synthetic Zeolite-twenty-three |
| TON | Theta-1 (one) | |
| TSC | Tschörtnerite | Jochen Tschörtner, finder of the mineral |
| VFI | VPI-5 (five) | Virgina Polytechnic Institute-five |
| VSV | VPI-7 (seven) | Virgina Polytechnic Institute-seven |
| ZON | ZAPO-M1 (one) | (Zn, Al)PO$_4$-Mulhouse-one |

Further, the size of molecular sieve material can vary, including the diameter of pellets if that is the form in which they are used. For example, in preferred embodiments of the present invention, smaller pellets are preferred to increase surface area available for molecular capture or transport. For example, a 1/16" diameter pellet is used in one preferred embodiment.

The term "microwave signals" is used to encompass all waves that travel from 1 Mhz up to and including infrared frequencies.

The term "electromagnetic characteristics" includes electrical and/or magnetic characteristics.

The terms "absorbent" and "adsorbent" are used throughout this specification, and are intended to broadly refer to the sequestration or capture of molecules or materials, and not necessarily to the limited ideas of surface or interior capture of molecules or materials. In general, the terms "absorbent" and "adsorbent" are intended to cover any of the ways that molecular sieve materials capture or contain or restrain or separate molecules from other types of molecules, such as water from oil.

An important advantage of the preferred embodiments is that the desiccant or sorbent material fills a relatively high fraction of the volume of the analysis bottle. This means that the electrical measurement stage will be strongly affected by changes in the electrical properties of the desiccant or sorbent, as opposed to the crude oil (or other fluid) being measured. (The electrical characteristics of the fluid itself can be strongly affected by emulsion characteristics, including droplet size and structure and the continuous phase if any, as well as salinity or other contaminants.)

Another important advantage of the preferred embodiments is that it provides a field-usable electrical assay technique that is fairly insensitive to emulsion properties (e.g. droplet size) and the changing density of the oil.

Modifications and Variations

As will be recognized by those skilled in the art, the innovative concepts described in the present application can be modified and varied over a tremendous range of applications, and accordingly the scope of patented subject matter is not limited by any of the specific exemplary teachings given.

In one embodiment, the present invention comprises equipment suitable for use in field testing, such as an easily-assembled kit of limited weight. In one preferred embodiment, such a field test kit weighs less than three pounds, and includes a microwave oscillator circuit, preferably housed in aluminum, a container for holding molecular sieve and a sample, and other equipment for preferably siphoning the sample through the molecular sieve.

In preferred embodiments, the present invention uses an oscillator system, such as an electrical oscillator system, and more specifically a microwave oscillator system. The exact frequency range of the oscillator can vary from implementation to implementation, and the examples given herein of a microwave oscillator are not intended to limit the invention to only those frequencies. Other frequencies that suitably interact with a sample in such a way that changes in the signal can be detected, such as by measuring scattering parameters. For example, in a load-pulled system, the frequency of the oscillator is affected by the sample, which changes the frequency at which the oscillator oscillates. Alternately, transmitted, reflected, and/or incident waves can be affected by the probed material and detected. In such examples, the permittivity of the system seen by the oscillator changes when the sample is introduced, and this change is detected via measuring the scattering parameters, for example. Though we herein characterize the change in the tested system as a change in permittivity, other characterizations are also possible and within the scope of the present invention.

One advantage of the present invention includes a decrease in error for determining, for example, the water and sediment content of a crude oils sample. Human operators can damage equipment, ruin calibration or settings, and influence the apparatus in other ways when handling sensitive testing equipment in the field. In the present invention, pre-packaged molecular sieves and the general hardiness and simplicity of the testing process and apparatus reduce human actions that must be taken in order to obtain an estimate of the water and sediment content in a sample. Further, a field test kit of the present innovations requires no trained technician for operation, and can be safely and effectively used by unskilled operators.

In one embodiment, the present invention allows testing of, for example, crude oil as it is in transport or exchanging possession, ownership, crossing political or legal boundaries, containers, etc. For example, crude oil unloaded from a ship to a new political boundary often requires an assessment of the actual amount of oil, which in turn requires an assessment of the amount of water in the offloaded liquid. The innovations of the present application provide an easy and effective means of providing the necessary information.

In yet another embodiment, the innovations herein described are used to test other materials. For example, the methanol in a solvent, or hexane in a solvent, or ketones in a solvent could be characterized using innovations of the present application.

In yet another embodiment, a "patch probe" is implemented having only a surface area of molecular sieve material exposed to absorb liquids or molecules from a tested material.

Due to the fact that molecular sieves can adsorb huge quantities of water, purging the sample and leaving the molecular sieves in the chamber could allow more analyses to be performed without changing the molecular sieves if the unit is properly calibrated. The same molecular sieves could then be used until they approach saturation.

The same package may be used for transporting and loading the sample in the microwave measurement system.

Different testing packages may be used depending on the pH of the sample and the solvent used (at least for special applications, e.g. a Teflon or glass bottle for hot solvents).

The analysis bottle may be resealed for convenient disposal of hazardous solvents. This would help in the transportation of the sample titer to the hazardous waste disposal through the laboratory ambient.

To minimize disposal and avoid contamination of the next sample, a sample port with a backpurge or flush-through maybe used to blow back the sample into the main tank.

It is also noted that the present innovations preferably occur in a non-equilibrium system, though the molecular sieve and tested material can of course be tested under equilibrium conditions in less preferred embodiments.

In a further alternative embodiment, the analysis bottle can already be prefilled with the desiccant or sorbent material. Thus, the analysis bottle itself hermetically protects the zeolite, or other desiccant or sorbent, from moisture contamination before the sample is introduced.

In a further alternative embodiment, the beads of the zeolite, or other desiccant or sorbent, can be fused or glued into a rigid mass with open pores. This permits more certainty that absorbent material will not be lost during transfer into the bottle. However, this embodiment makes it more difficult to fill the bottle, so this embodiment may be more advantageous with vacuum filling methods.

Note that, in some embodiments, it is not strictly necessary for the desiccant or sorbent to fill the measuring bottle, as long as the volume of strong electric-field coupling to the electrical probe(s) is filled.

In a further class of alternative embodiments, a precalibrated bottle and desiccant or sorbent can be used for moisture assay of dry materials, such as flour or other stocks for food or feed or pharmaceutical preparation.

In some embodiments, it is preferable to shake or stir the sample just before insertion into the measurement unit to minimize the effect of separations may occur in the liquid phase.

None of the description in the present application should be read as implying that any particular element, step, or function is an essential element which must be included in the claim scope: THE SCOPE OF PATENTED SUBJECT MATTER IS DEFINED ONLY BY THE ALLOWED CLAIMS. Moreover, none of these claims are intended to invoke paragraph six of 35 USC section 112 unless the exact words "means for" are followed by a participle.

The claims as filed are intended to be as comprehensive as possible, and NO subject matter is intentionally relinquished, dedicated, or abandoned.

What is claimed is:

1. A method for determining a water content and a sediment content of a fluid, the method comprising:

receiving the fluid to an apparatus comprising a filter and a graduated sight glass;

determining the sediment content of the fluid using the graduated sight glass; receiving the fluid from the apparatus and into an analysis bottle containing an absorbent material;

determining the water content of the fluid by measuring an expanded volume of the absorbent material.

2. The method of claim 1, wherein the analysis bottle is foil sealed.

3. The method of claim 1, wherein the absorbent material is polyacrylic acid.

4. The method of claim 1, wherein the method further comprises stirring the fluid as it is transferred from the apparatus to the analysis bottle.

5. The method of claim 1, wherein the fluid comprises oil with an unknown amount of water.

* * * * *